US00PP28414P2

(12) United States Plant Patent
Koekkoek

(10) Patent No.: US PP28,414 P2
(45) Date of Patent: Sep. 19, 2017

(54) ***ALSTROEMERIA* PLANT NAMED 'TESMOONLI IMP.'**

(50) Latin Name: *Alstroemeria hybrida*
Varietal Denomination: Tesmoonli imp.

(71) Applicant: Arthur N. J. Koekkoek, Alkmaar (NL)

(72) Inventor: Arthur N. J. Koekkoek, Alkmaar (NL)

(73) Assignee: VOF Hortipartners, Heerhugowaard (NL)

( * ) Notice: Subject to any disclaimer, the term of this patent is extended or adjusted under 35 U.S.C. 154(b) by 0 days.

(21) Appl. No.: 14/999,642

(22) Filed: Jun. 8, 2016

(51) Int. Cl.
*A01H 5/02* (2006.01)

(52) U.S. Cl.
USPC ..... Plt./309

(58) Field of Classification Search
USPC ..... Plt./309
CPC ..... A01H 5/0211
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Tesmoonli imp.', characterized by its broadly upright plant habit; relatively short flowering stems; sturdy and strong plants; low to moderately vigorous growth habit; numerous large white-colored flowers with purple-colored centers; and good garden performance.

1 Drawing Sheet

Botanical designation: *Alstroemeria hybrida.*
Cultivar denomination: 'TESMOONLI imp.'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tesmoonli imp.'.

The new *Alstroemeria* plant is a product of a planned breeding program conducted by the Inventor in Heerhugowaard, The Netherlands. The objective of the breeding program is to create new potted garden *Alstroemeria* plants with numerous attractive flowers and flower continuously during the flowering season.

The new *Alstroemeria* plant originated from a cross-pollination made by the Inventor in Heerhugowaard, The Netherlands in May, 2010 of a proprietary selection of *Alstroemeria hybrida* identified as code number Pf908, not patented, as the female, or seed, parent with a proprietary selection of *Alstroemeria hybrida* identified as code number Ze6176x007, not patented, as the male, or pollen, parent. The new *Alstroemeria* plant was discovered and selected by the Inventor as a single flowering plant from within the progeny of the stated cross-pollination in a controlled greenhouse environment in Heerhugowaard, The Netherlands in March, 2011.

Asexual reproduction of the new *Alstroemeria* plant by root divisions in a controlled greenhouse environment in De Kwakel, The Netherlands since August, 2011 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Tesmoonli imp.'. These characteristics in combination distinguish 'Tesmoonli imp.' as a new and distinct *Alstroemeria* plant:

1. Broadly upright plant habit; relatively short flowering stems.
2. Sturdy and strong plants; low to moderately vigorous growth habit.
3. Numerous large white-colored flowers with purple-colored centers.
4. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are not as compact as plants of the female parent selection.
2. Plants of the new *Alstroemeria* have smaller leaves than plants of the female parent selection.

Plants of the new *Alstroemeria* can be compared to plants of the male parent selection. Plants of the new *Alstroemeria* differ from plants of the male parent selection in the following characteristics:

1. Plants of the new *Alstroemeria* are shorter than plants of the male parent selection.
2. Plants of the new *Alstroemeria* have smaller leaves than plants of the male parent selection.
3. Plants of the new *Alstroemeria* have smaller flowers than plants of the male parent selection.

Plants of the new *Alstroemeria* can be compared to plants of the *Alstroemeria hybrida* 'Tespassion', disclosed in U.S. Plant Pat. No. 25,369. In side-by-side comparisons, plants of the new *Alstroemeria* differ primarily from plants of 'Tespassion' in the following characteristics:

1. Plants of the new *Alstroemeria* have larger flowers than plants of 'Tespassion'.
2. Outer perianth flower segments of plants of the new *Alstroemeria* are more deeply emarginate than outer perianth flower segments of 'Tespassion'.
3. Plants of the new *Alstroemeria* and 'Tespassion' differ in flower color as plants of 'Tespassion' have white to light purple-colored flowers with darker purple-colored centers.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant.

The photograph comprises a side perspective view of typical flowering plants of 'Tesmoonli imp.' grown in a container.

DETAILED BOTANICAL DESCRIPTION

Plants used for the aforementioned photograph and following observations and measurements were grown during the spring in 24-cm containers in a glass-covered greenhouse in De Kwakel, The Netherlands. During the production of the plants, day temperatures ranged from 12° C. to 17° C., night temperatures averaged 12° C. and light levels averaged 7,000 lux. Plants used in the photograph were 15 weeks old and plants used for the description were 18 weeks old. Color references are made to The Royal Horticultural Society Colour Chart, 2015 Edition, except where general terms of ordinary dictionary significance are used.

Botanical classification: *Alstroemeria hybrida* 'Tesmoonli imp.'.

Parentage:

*Female, or seed, parent*.—Proprietary selection of *Alstroemeria hybrida* identified as code number Pf908, not patented.

*Male, or pollen, parent*.—Proprietary selection of *Alstroemeria hybrida* identified as code number Ze6176x007, not patented.

Propagation:

*Type*.—By root divisions.

*Time to produce a rooted young plant, summer*.—About seven weeks at temperatures about 20° C.

*Time to produce a rooted young plant, winter*.—About eight weeks at temperatures about 16° C.

*Root description*.—Fibrous and fleshy; thick to thin; typically white in color, actual color of the roots is dependent on substrate composition, water quality, fertilizer type and formulation, substrate temperature and physiological age of roots.

*Rooting habit*.—Freely branching; medium density.

*Rhizome length*.—About 23 cm.

*Rhizome diameter*.—About 5 mm.

*Rhizome texture*.—Smooth, glabrous.

*Rhizome color*.—Close to 160D.

Plant description:

*Plant and growth habit*.—Herbaceous perennial; broadly upright plant habit with relatively short flowering stems, flattened globular; freely branching habit with about 26 primary lateral branches developing per plant; sturdy and strong plants; low to moderately vigorous growth habit.

*Plant height, soil level to top of foliar plane*.—About 20.2 cm.

*Plant height, soil level to top of floral plane*.—About 24.1 cm.

*Plant diameter* (*area of spread*).—About 41.7 cm.

Lateral branch description:

*Aspect*.—Mostly upright to about 70° from vertical.

*Length*.—About 13.9 cm.

*Diameter*.—About 6 mm.

*Internode length*.—About 1 cm.

*Strength*.—Moderately strong.

*Texture and luster*.—Smooth, glabrous, waxy; matte.

*Color, developing*.—Close to 145A; at the internodes, close to 144A.

*Color, developed*.—Close to 144A; waxy cuticle, close to 142B.

Leaf description:

*Arrangement*.—Alternate; below the peduncles in a single whorl; simple.

*Length*.—About 6.6 cm.

*Width*.—About 2.6 cm.

*Shape*.—Ovate to narrowly ovate; twisting.

*Apex*.—Acute.

*Base*.—Cuneate.

*Margin*.—Entire.

*Texture and luster, upper surface*.—Smooth, glabrous; matte.

*Texture and luster, lower surface*.—Smooth, glabrous; slightly glossy.

*Venation pattern*.—Parallel.

*Color*.—Developing leaves, upper surface: Surface faces downwards; close to 138A. Developing leaves, lower surface: Surface faces upwards; slightly darker than 143A. Fully expanded leaves, upper surface: Surface faces downwards; close to between 147B and 191A; venation, similar to lamina. Fully expanded leaves, lower surface: Surface faces upwards; darker than between 141A and 143A; venation, darker than between 141A and 143A.

*Petioles*.—Length: About 2.1 cm. Diameter: About 2 mm by 8 mm. Texture and luster, upper surface: Smooth, glabrous; matte. Texture and luster, lower surface: Smooth, glabrous; moderately glossy. Color, upper surface: Close to 143A to 143B. Color, lower surface: Close to 138A.

Flower description:

*Flower type and habit*.—Single zygomorphic flowers arranged in terminal umbels; flowers face mostly outwardly to slightly upright; perianth segments separate; freely flowering habit with about nine flowers per inflorescence and about 230 flowers developing per plant during the flowering season.

*Natural flowering season*.—Plants begin flowering about eight weeks after planting; flowering continuous from late spring into the summer in The Netherlands.

*Fragrance*.—None detected.

*Flower longevity on the plant*.—About ten days; flowers not persistent.

*Flower buds*.—Length: About 3 cm. Diameter: About 1.4 cm. Shape: Obovate. Texture and luster: Smooth, glabrous; matte. Color: Close to 145C to 145D; towards the apex, close to 143B to 143C; venation, close to 143A.

*Umbel height*.—About 10.4 cm.

*Umbel diameter*.—About 13.2 cm.

*Flower diameter* (*horizontal*).—About 7.4 cm.

*Flower length* (*vertical*).—About 6.9 cm.

*Flower depth* (*height*).—About 6.6 cm.

*Perianth*.—Arrangement: Six arranged in two whorls, each whorl with two lateral and one median segments. Size, inner perianth: Length, lateral segments: About 6.8 cm. Width, lateral segments: About 2.9 cm. Length, median segment: About 5.5 cm. Width, median segment: About 2.9 cm. Size, outer perianth: Length, lateral segments: About 6.1 cm. Width, lateral segments: About 4.2 cm. Length, median segment: About 6.3 cm. Width, median segment: About 4.3 cm. Shape, inner perianth, lateral and median segments: Oblanceolate. Shape, outer perianth, lateral and median segments: Obcordate. Apex, inner perianth, lateral and median segments: Abruptly acute. Apex, outer perianth, lateral and median segments: Emarginate. Base, inner perianth, lateral and median segments: Narrowly cuneate. Base, outer perianth, lateral and median segments: Long cuneate. Margin, inner perianth, lateral and median segments: Entire. Margin, outer perianth, lateral and median segments: Towards the apex, finely serrate; towards the base, entire. Texture, inner and outer perianths, lateral and median segments, upper and lower surfaces: Smooth, glabrous. Luster, inner perianth, lateral and median segments, upper surface: Matte. Luster, inner perianth, lateral and median segments, lower surface: Slightly glossy. Luster, outer perianth, lateral and median segments, upper surface: Matte. Luster, inner perianth, lateral and median segments, lower surface: Slightly glossy. Color, inner perianth: When opening, lateral segments, upper surface: Close to NN155A; fading proximally to close to 69C; central blotch, lighter than 4D; spots, close to N186C and 200A; apex, close to 143B. When opening, median segment, upper surface: Close to NN155A; fading proximally to close to 69C; spots, close to N186C and 200A; apex, close to 143B. When opening, lateral segments, lower surface: Close to 155C; fading proximally to lighter than 186D; central blotch, close to 157C; spots, close to N200C; apex, close to 143B. When opening, median segment, lower surface: Close to NN155A; fading proximally to lighter than 186D; spots, close to 183D; apex, close to 143B. Fully opened, lateral segments, upper surface: Close to NN155A; fading proximally to close to 76B; central blotch, close to 8C to 8D; spots and stripes, close to N186C and 200A; apex, close to 143B. Fully opened, median segment, upper surface: Close to NN155C; fading proximally to close to 76B to 76C; spots and stripes, close to N186C; apex, close to 143B. Fully opened, lateral segments, lower surface: Close to NN155C; fading proximally to close to 76B; spots and stripes, close to N200C; apex, close to 143B. Fully opened, median segment, lower surface: Close to NN155C; fading proximally to close to 76B to 76C; spots and stripes, lighter than 183D; apex, close to 143B. Color, outer perianth: When opening, lateral segments, upper surface: Distally, close to NN155C; proximally, close to 76C tinged with close to N75C; apex, close to 143A. When opening, median segment, upper surface: Distally, close to NN155C; proximally, close to 76C tinged with close to N80C; apex, close to 143A. When opening, lateral segments, lower surface: Distally, close to NN155B; proximally, close to 186D; apex, close to 143A to 143C. When opening, median segment, lower surface: Distally, close to NN155B; proximally, close to 186C to 186D; apex, close to 143A to 143C. Fully opened, lateral and median segments, upper surface: Distally, close to NN155D; proximally, close to 76C; apex, close to 143A and 147D. Fully opened, lateral and median segments, lower surface: Distally, close to NN155D; proximally, close to 76B; apex, close to 143A.

*Pedicels*.—Length: About 1.1 cm. Diameter: About 2.5 mm. Strength: Moderately strong. Angle: About 7.5° from stem axis. Texture and luster: Smooth, glabrous; slightly glossy. Color, upper and lower surfaces: Close to 143C.

*Reproductive organs*.—Stamens: Quantity per flower: Six. Filament length: About 3.9 cm. Filament color: Close to 75D; towards the base, close to N155B. Anther shape: Oblong. Anther length: About 7.5 mm. Anther color: Close to between 151B and 195A. Pollen amount: Moderate. Pollen color: Close to 202C. Pistils: Quantity per flower: One. Pistil length: About 4.9 cm. Style length: About 4.7 cm. Style color: Close to N82D; towards the base, close to N155B. Stigma shape: Tri-parted; parts, club-shaped, curved. Stigma color: Close to N82D. Ovary color: Close to 13 8B; towards the apex, close to 138A.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate high temperatures of about 35° C. and to be suitable for USDA Hardiness Zones 7 to 10.

It is claimed:

1. A new and distinct *Alstroemeria* plant named 'Tesmoonli imp.' as illustrated and described.

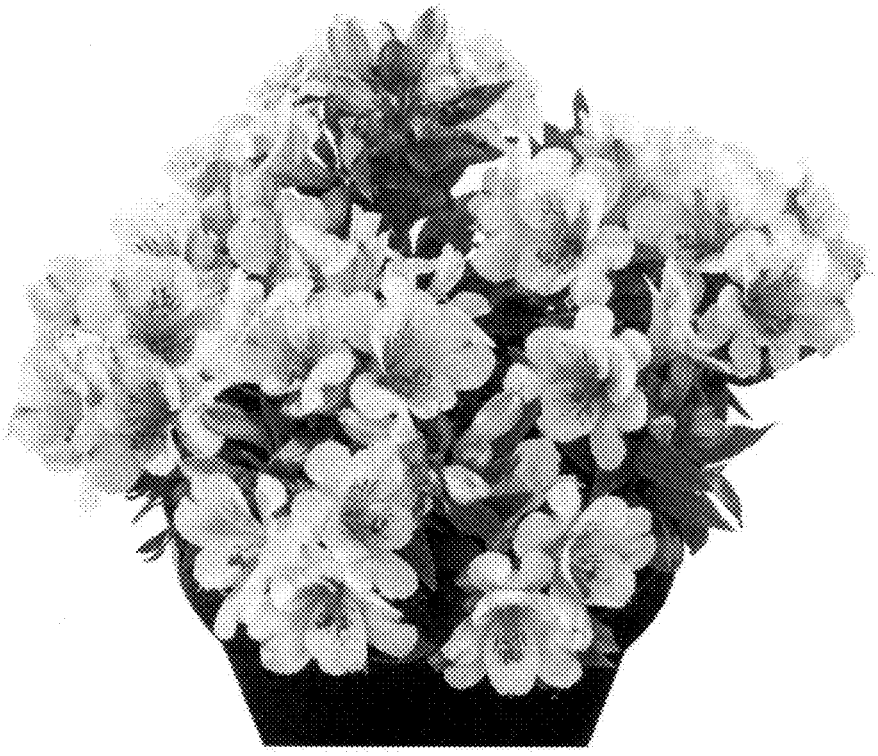

* * * * *